United States Patent
Douglas et al.

(10) Patent No.: US 6,673,440 B2
(45) Date of Patent: Jan. 6, 2004

(54) SUBCUTANEOUS INJECTION SET TUBING WITH SOLVENT BONDING

(75) Inventors: Joel Sterling Douglas, Los Altos Hills, CA (US); Robert Louis Hugo, Gilroy, CA (US); Hiroshi Nomvra, Shorewood, MN (US)

(73) Assignee: Sterling Medivations, Inc., Norcross, GA (US)

( * ) Notice: Subject to any disclaimer, the term of this patent is extended or adjusted under 35 U.S.C. 154(b) by 0 days.

(21) Appl. No.: 09/944,229

(22) Filed: Aug. 30, 2001

(65) Prior Publication Data
US 2002/0055722 A1 May 9, 2002

Related U.S. Application Data

(60) Provisional application No. 60/251,087, filed on Dec. 4, 2000, provisional application No. 60/248,354, filed on Nov. 15, 2000, and provisional application No. 60/246,374, filed on Nov. 6, 2000.

(51) Int. Cl.[7] .......................... B32B 7/12; B32B 27/08; B32B 27/30; B32B 27/32
(52) U.S. Cl. .................... 428/336; 156/272.6; 156/293; 156/294; 156/308.6; 156/309.3; 427/2.28; 427/488; 427/491; 428/36.9; 428/36.91; 428/422; 428/518; 428/520; 428/522
(58) Field of Search .............................. 156/272.6, 293, 156/294, 308.6, 309.3; 427/2.28, 488, 491; 428/36.9, 36.91, 336, 422, 500, 518, 520, 522

(56) References Cited

U.S. PATENT DOCUMENTS

| | | |
|---|---|---|
| 4,403,990 A | 9/1983 | Garver, Sr. |
| 4,531,937 A | 7/1985 | Yates |
| 4,723,947 A | 2/1988 | Konopka |
| 4,755,173 A | 7/1988 | Konopka et al. |
| 5,522,803 A | 6/1996 | Teissen-Simony |
| 5,522,832 A | 6/1996 | Kugo et al. |
| 5,523,347 A | 6/1996 | Kneafsey et al. |
| 5,567,266 A | 10/1996 | Liu |
| 5,610,251 A | 3/1997 | Kneafsey et al. |
| 5,643,982 A | 7/1997 | Liu |
| 5,749,956 A | 5/1998 | Fisher et al. |
| 5,811,473 A | 9/1998 | Ramos et al. |
| 6,056,718 A | 5/2000 | Funderburk et al. |

FOREIGN PATENT DOCUMENTS

| | | |
|---|---|---|
| EP | 0 256 694 A1 | 2/1988 |
| WO | 88/03816 | 6/1988 |

*Primary Examiner*—D. S. Nakarani
(74) *Attorney, Agent, or Firm*—Burns Doane Swecker & Mathis, L.L.P.

(57) ABSTRACT

The infusion set comprises of a connecting tube of polyethylene which is treated to form a wetable surface or treated with a primer and then bonded to a PVC hub by using solvent adhesive to solvent bond the low density polyethylene tubing or Teflon tubing to a PVC hub. The surface treatment methods include a methane plasma surface that is applied to tubing in a continuous manner and alternatively a primer that is applied locally and dried prior to applying the adhesive. Both techniques form a strong and resilient bond for the infusion needle and tube when assembled to the PVC hubs.

5 Claims, 5 Drawing Sheets

SUBCUTANEOUS INJECTION SET TUBING WITH SOLVENT BONDING

The present application is related and claimed priority to U.S. application Ser. No. 60/251,087, filed Dec. 04, 2000, by Joel Douglas and Hiroshi Nomura, U.S. application Ser. No. 60/246,374, filed Nov. 06, 2000, by Joel Douglas, U.S. application Ser. No. 60/248,354, filed Nov. 15, 2000, by Joel Douglas and Hiroshi Nomura the entire contents of each of which is incorporated by reference herein.

BACKGROUND OF THE INVENTION

FIELD OF THE INVENTIN

The present invention relates generally to injection devices for use with an external infusion system whereby a desired fluid is subcutaneously delivered to a patient, and more particularly to a disposable injection set for delivering insulin to the patient which injection set is conveniently and inexpensively manufactured of materials which will not cause a reaction with insulin passing there through, thereby avoiding the adverse results of such an insulin reaction.

Generally, in order to subcutaneously dispense a fluid from an external source to a patient, the distal end of a hollow needle or soft Teflon cannula is inserted through the skin of the patient, thereby providing a passageway to the desired subcutaneous injection location under the skin of the patient. The proximal end of the hollow needle or soft Teflon cannula located externally of the skin of the patient is connected to one end of a tube, the other end of which is connected to the external source of the fluid to be injected, typically with a luer connector made of hard PVC (polyvinyl chloride) or PC (polycarbonate) and which may be easily connected by merely inserting the mating connectors together and twisting to lock them together.

A preferred technique for connecting the tube to the needle involves the molding of a hard PVC or PC segment around the proximal end of the needle or fitting it to a soft Teflon cannula, and then utilizing flexible PVC tubing which may be solvent bonded to the hard PVC segment molded around the proximal end of the needle. Solvent bonding is preferred because of the relative ease of the solvent bonding operation, the strength and durability of the solvent bond, and the inexpensive cost of solvent bonding. Since such infusion sets are disposable, cost and acceptable shelf life are important criteria by which such an infusion set will be judged.

The recent popularity of insulin infusion pumps as an alternative to multiple daily injections for insulin-dependent diabetics requires the use of such an injection set to deliver insulin from a small, portable insulin infusion pump to the subcutaneous injection location. It has been determined that there exists a substantial problem with the use of injection sets as described above in that flexible PVC is not completely insulin compatible. This is in contrast to hard PVC, which is perfectly safe for use with insulin. While the exact nature of the reaction exhibited by insulin in contact with flexible PVC has not been determined with certainty, it is believed that the insulin, which is pH sensitive, reacts with $CO_2$, the flow of which there through is not inhibited by flexible PVC. In addition, the large quantities of plasticizer used in flexible PVC may result in a leaching problem when used with insulin.

Since flexible PVC is not a barrier for $CO_2$, the $CO_2$ which flows through the flexible PVC tubing will react with the insulin, causing the insulin to aggregate and to precipitate out of solution. Such precipitation of the insulin will likely cause clotting and blockage in the tube or in the needle, thereby inhibiting the flow of insulin to the subcutaneous depot.

Heat will also accelerate the clotting process of insulin in flexible PVC tubing without the pH change caused by $CO_2$. The reason for this has not been finally determined, but it may be due to zinc in the insulin forming zinc chloride. In any event, heat will further compound the situation faced by delivery of insulin through flexible PVC tubing.

The amount of insulin exiting the injection set will therefore vary considerably, with portions of the insulin becoming attached to the interior of the tube and eventually coating the interior of the tube even if blockage does not occur. Over time, the situation will improve somewhat assuming blockage of the tube per se does not occur, but the amount of insulin actually delivered to the patient will vary considerable even with the best of circumstances. It may therefore be appreciated that the use of a flexible PVC tubing injection set to deliver insulin from an insulin infusion pump is neither desirable nor medically acceptable.

It should also be noted that other substances exhibit reactions when delivered through flexible PVC tubing. Lipids and proteins have adverse reactions with flexible PVC delivery systems, and nitroglycerin also reacts to some degree with a flexible PVC environment.

Several problems have arisen with the use of epoxy bonded polyethylene infusion sets, all of which are due to the relative disadvantage of the epoxy bonding process to the solvent bonding process. First of all, an epoxy bond is simply not as strong as a solvent bond. Secondly, epoxy bonds have substantial aging problems, which limit shelf life of the injection set. Since the epoxy bond loses its mechanical bonding properties over time, the injection set will become less sturdy, with the potential for the tubing coming loose from the needle increasing substantially over time. Thirdly, batch control of epoxy used in epoxy bonding is time consuming and cumbersome. Finally, epoxy bonding or "potting" is a more expensive process than solvent bonding, resulting in a product having an economic disadvantage relative to a product made by solvent bonding.

One solution to the problem of insulin aggregating and precipitating out of solution is to use Polyethylene as a barrier to $CO_2$, and the major problem of $CO_2$ passing through the tubing is thereby eliminated. Additionally, the problem of clotting of the insulin due to heat is also substantially minimized.

However, polyethylene is not solvent bondable as is flexible PVC, and a substantial problem in manufacturing injection sets using polyethylene has arisen. The preferred method to date has been to use epoxy to "pot" the polyethylene tubing to the needle, without using a hard PVC segment molded onto the needle. Although the hard PVC segment could be used, since polyethylene is not susceptible to solvent bonding it would be necessary to epoxy the polyethylene tubing to the hard PVC segment, resulting in a higher cost injection set.

Another preferred technique for connecting the tube to the needle involves the molding of a hard PVC or PC segment around the proximal end of the needle or fitting it to a soft Teflon cannula, and then utilizing flexible co-extruded tubing made from a Low Density polyethylene (LDPE) inner tube and a PVC outer tube which may be solvent bonded to the hard PVC segment molded around the proximal end of the needle. Solvent bonding is preferred because of the relative ease of the solvent bonding operation, the strength and durability of the solvent bond, and the inexpensive cost of solvent bonding. The LDPE inner portion provides a suitable barrier for the $CO_2$. Since such infusion sets are disposable, cost and acceptable shelf life are important criteria by which such an infusion set will be judged and the incremental cost of the co-extruded tube is overcome by the elimination of the epoxy bonds at the joint.

It is thereby apparent that there exists a substantial need for an injection set for delivery of insulin (or other fluids exhibiting reactions when flowed through flexible PVC tubing), which injection set utilizes polyethylene tubing to inhibit reaction and subsequent degradation of insulin flowing there through. It is a primary objective that the injection set be susceptible to manufacture by solvent bonding, thereby resulting in a superior mechanical bond having great strength and excellent shelf life without incurring the additional cost of co-extruded tubing.

It is also desirable that the improved injection set be of economical manufacture, to thereby result in an inexpensive disposable product which may be easily marketed. Finally, it is desirable that the improved injection set achieve the aforementioned advantages and solve the previously mentioned disadvantages without substantial disadvantage.

The present invention relates to an infusion set for an intermittent or continuous administration of a therapeutical substance, such as insulin. It is generally related to injection devices for use with an external infusion system whereby a desired fluid is subcutaneously delivered to a patient, and more particularly to a disposable injection set for delivering insulin to the patient which injection set is convenient, comfortable and inexpensively manufactured. The invention also relates generally to injection devices for use with an external infusion system wherein a desired therapeutic fluid needs to remain sterile and is subcutaneously delivered to a patient, and more particularly to a disposable subcutaneous injection set having a soft or metal cannula which is inserted approximately normal to the skin to a desired subcutaneous injection level to deliver the therapeutic fluid with a minimum of discomfort and bother to the patient.

Unfortunately, several problems associated to infusing fluids into the patient as described above are usually encountered. Most of the systems the patients use currently are fastened together using epoxy joins and most recently, the infusions sets are manufactured with a co-extruded tubing which facilitates solvent bonding. However, the epoxy joins are subject to becoming brittle and limiting the shelf life of the infusion set and when a co-extruded tube is used with solvent bonding techniques, the co-extruded or tri-extruded tube adds considerable cost.

The recent popularity of insulin infusion pumps as an alternative to multiple daily injections for insulin-dependent diabetics requires the use of an injection set to deliver insulin from a small, portable insulin infusion pump to the subcutaneous injection location. However, the current devices do not provide the benefit of a simple and low cost bonding method.

A number of solutions attempting to address these problems have been offered. The disclosures of these patents are included by reference. For example, it is known in the art to insert a soft cannula into the patient rather than a stiff, hard needle or equivalent device. Such a device is shown in U.S. Pat. No. 4,723,947, to Konopka, which describes an insulin infusion catheter that is configured from a dual tube and attached to the infusion mechanism with a luer lock fitting.

Additionally the following patents do not specify the connecting means but provide different configurations which are achievable at a lower cost when used with the current invention. U.S. Pat. No. 4,755,173, to Konopka, et al. provides for a soft cannula tip for insertion into the patient. U.S. Pat. No. 4,531,937, to Yates. Provides for a soft cannula that is much more comfortable to the patient than such rigid devices. U.S. Pat. No. 5,522,803 Teissen-Simony provides for a soft catheter system with a membrane situated in front of the soft catheter. U.S. Pat. No. 6,056,718 Fundedburk, et al. describes a similar device to U.S. Pat. No. 5,522,803 but uses a septum as the sealing means.

Advancements in solvent bonding have also been achieved. U.S. Pat. No. 5,523,347, Kneafsey, et al describes a one part air activated polymerizable composition having an activator system.

U.S. Pat. No. 5,610,251, Kneafsey, et al describes a polymerisable composition using an air-activated latent initiator system of hydrogenated pyridine compound and acid.

U.S. Pat. No. 5,643,982, Liu describes a non-ozone depleting, non-flammable co-solvent composition useful as a carrier for actives such as accelerators, catalysts, initiators, activators and other primer materials for use as adhesive promoter compositions in combination with adhesive compositions. The co-solvent compositions include an azeotropic solution of a perfluorocarbon and an alkylsiloxane.

U.S. Pat. No. 5,567,266, Liu describes a non-environmentally hazardous, non-volatile adhesive promoter composition useful in promoting the cure and/or enhancing adhesion of adhesives and for use in combination with adhesive bond polymerization. The promoter composition is a combination of a fluid carrier that remains substantially present during the curing of an adhesive composition and an active component capable of promoting the cure and/or enhancing adhesion of the adhesive and being miscible in the fluid carrier.

U.S. Pat. No. 5,749,956, Fisher, et al describes a non-ozone depleting, non-flammable co-solvent composition useful as a carrier for actives such as accelerators, catalysts, initiators, activators and other primer materials for use as adhesive promoter compositions in combination with adhesive compositions. The co-solvent compositions include an azeotropic solution of a halogenated compound and an aliphatic or aromatic hydrocarbon compound.

U.S. Pat. No. 5,811,473, Ramos, et al describes a primer activator composition useful in cleaning and activating metallic surfaces in preparation for use with an anaerobic adhesive. The composition contains a non-combustible, non-ozone depleting, liquid polyfluoroalkane having at least one carbon-hydrogen bond, preferably a C.sub.4–10 dihydro- or trihydro-polyfluoroalkane; an alkanol which is capable of forming an azeotropic mixture with the polyfluoroalkane, preferably a C.sub.1–6 alkanol, such as n-butanol; a transition metal compound, preferably a copper compound; and optionally, an amine co-activator.

The disclosures of each of the above patent specifications are incorporated herein by reference in their entirety.

However, these primers require the manufacture to apply them in a first operation and then apply the solvent adhesive. This is an additional step that can lead to manufacturing errors and the shearing strength of these bonds result in the need to modify the socket for bonding to insure adequate shearing strength. The current ISO standards require significant resistance to pull testing for the bonded joints. The infusion sets also use small diameter tubing which limits the surface area for the bonding process and the need to insure a comfortable and small package make it necessary to understand the bonding properties vs. the engagement of the tubing to the PVC or PC socket.

The present invention also relates generally to injection devices for use with an external infusion system whereby a desired fluid is subcutaneously delivered to a patient, and more particularly to a disposable injection set for delivering insulin to the patient which injection set is conveniently and inexpensively manufactured of materials which will not cause a reaction with insulin passing there through, thereby avoiding the adverse results of such an insulin reaction.

A preferred technique for connecting the tube to the needle involves the molding of a hard PVC segment around the proximal end of the needle, and then utilizing flexible PVC tubing which may be solvent bonded to the hard PVC segment molded around the proximal end of the needle. Solvent bonding is preferred because of the relative ease of the solvent bonding operation, the strength and durability of the solvent bond, and the inexpensive cost of solvent bonding. Since such infusion sets are disposable, cost and acceptable shelf life are important criteria by which such an infusion set will be judged.

However, the first means of the invention utilizes a means of inserting the needle into the tube, applying a polymer based primer to the LDPE tube and to the PVC socket, allowing it to dry momentarily and then applying a solvent adhesive to the connecting LDPE tube and inserting it into the molded piece where it is solvent bonded to the assembly. The solvent bonding of the needle caused by this procedure seals the needle and tube to the PVC hub. The second means of the invention replaces the polymer based primer with a methane plasma coating on the outer diameter of the LDPE tubing. The plasma discharged layer of Methane on the outer diameter of the tube forms a wetable surface on the outer diameter of the tube and allows the assembly to be bonded together using solvent adhesives. The cost savings are considerable. Co and triaxial extruded tubing of the prior art cost between 4–5 times the cost of the current connecting tube used by our new invention.

A third aspect of the invention is the utilization of the plasma coating to form a wetable layer between Teflon tubing and other solvent bondable materials. The plasma coated layer being bonded to the Teflon tubing and bondable by a cyanoacrylate adhesive.

A fourth aspect of the invention is utilization of the plasma coating to form a wetable layer between Low Density Polyethylene (LDPE) sheet or parts and other solvent bondable materials. The plasma coated layer being bonded to the LDPE and bondable by a cyanoacrylate adhesive A fifth aspect of the invention is the utilization of the plasma coating to form a wetable layer between Teflon sheet or parts and other solvent bondable materials. The plasma coated layer being bonded to the Teflon and bondable by a cyanoacrylate adhesive.

In view of the above, it may be perceived that a substantial need exists for an injection set that combines the advantageous features of the devices discussed above, such as the use of a cannula for piercing a septum in the medication delivery, but without the disadvantages encountered by such devices, namely the difficulties associated with priming and sealing the devices, disconnecting and the comfort of the infusion set.

SUMMARY OF THE INVENTION

The present invention teaches a disposable injection set that offers the ability for the patient to infuse insulin or other medication without the problems of epoxy bonding of co-extrude tubing or medication degradation. The adhesive is selected from a set of solvent adhesives such as Loctite 4011, and the LDPE tubing is either primed with a primer such as Loctite 7701 or plasma treated with Methane and oxygen mixture forming a suitable surface on the tubing which is between 25 Å and 2000 Å thick for bonding polyethylene tubing to PVC or PC hubs. The adhesive needs to create the appropriate bond and be capable of being sterilized. The solvent needs to produce a secure joint that will not pass air or the infused liquid.

Furthermore the connecting tube can be formed from polyethylene or polypropylene that are relatively inert to the insulin being supplied to the patient and utilizes a process that will create a bond that is sealed from passage of air and medication.

The means of insuring this is to utilize a process that achieves a double containment and utilizes either a polymer primer or a Methane coating on the OD of the tubing that enables the solvent bonding of the tube to the PVC hub.

In the first embodiment the tubing is first treated on the OD with a primer such as Loctite 7701 or LDPE primer from Toagosei and the PVC or PC hub ID is also treated with the same primer. Loctite 7701 and the LDPE primer from Toagosei are solutions of aliphatic amine in Heptane solvent. The primer behaves like an activator and accelerates the cure speed of cyanoacrylate adhesives. This is not obvious because the instructions for the primer do not identify coating the ID of the solvent bondable hub. The solvent adhesive is applied to the OD of the tubing and the joint is bonded together by pushing the tubing into the socket and twisting the tube while inserting one revolution. This process provides a suitable bond between the tubing and the PVC or PC hub. The pull test results for the process described versus applying the primer to only the OD of the LDPE tubing and following the same procedure were 15 out of 15 bonds sealed correctly so they were leak tight vs. 3 out of 15 for the traditional process. However, to insure that the joint worked even with the modified process the dimensions of the socket and the fit of the tube had to meet the following dimensional requirements.

For tubing that has a needle inserted in the tube and the hub, such as an infusion cannula, the polyethylene tube ID must provide a radial force on the needle joint and the ID of the tube should be selected such that for a needle OD of 0.016 to 0.017 inches, the tube ID is 0.014 to 0.015 inches, and for a needle OD of 0.018 to 0.019 inches, the tube ID is 0.016 to 0.017 inches. This provides a slight press fit to the needle. The press fit of the needle caused by this procedure seals the needle to the inner tube and the solvent boding of the needle and tube to the PVC hub allows the assemble to be bonded together when the tubing is treated with primer. This reduces the cost of assembling the device and the cost of the molded pieces by eliminating the insert molding operations.

The next step is to apply the primer as described above to both the ID of the hub socket and the OD of the polyethylene tubing. A suitable primer is Loctite 7701 or Primer for LDPE bonding from Toagosei. The adhesive such as Loctite 4011, a cyanoacrylate adhesive, (any solvent base adhesive can be substituted that is capable of bonding the base material of the socket) must be applied and the join made up within 3 minutes of the application of the primer. The Loctite 4011 is an acceptable adhesive for this application. The length of application is again significant in order to provide a completely sealed part and prevent the leakage of either air or medication. The primer coated tubing joint does provide the same sealing characteristics as a PVC to PVC joint and the surface area required to produce a similar joint requires a minimum of area. The needle joint to the PVC requires an application length of at least 0.002 square inches of surface of the needle. For a 0.016 inch diameter needle the application length would have to be 0.050 inches sealing the needle to the PVC and the Polyethylene tubing to the PVC needs to have least 0.1 inches by 0.030 inches area to give an appropriate bond to prevent the joint from dislodging from the bond and to prevent leakage. For a 0.050-inch ID tube the minimum length of adhesive would be at least 0.020 inches long. To achieve a full strength bond the application would require a 0.050-inch depth for a 0.050-inch OD polyethylene tube. The ID of the PVC hub in the area of the needle cannot exceed 0.002 inches greater diameter than the needle and the ID of the PVC hub to the polyethylene tube cannot exceed 0.003 inches greater diameter than the assembled tube and bonded needle. If the dimensional requirements are not met the bond shear strength is not adequate to meet the ISO requirements and the tubing can be pulled out of the socket or the needle pulled out of the tube.

The press fit of the needle caused by this procedure seals the needle to the inner tube and the solvent boding of the needle and tube to the PVC hub allows the assemble to be bonded together when the tubing is treated with the primer. This reduces the cost of assembling the device and the cost of the molded pieces by eliminating the insert molding operations.

The second most preferred embodiment utilizes a plasma coating formed of methane gas on the outer diameter of the LDPE tubing. The plasma discharged layer of methane and oxygen on the outer diameter of the tube forms a wetable surface on the outer diameter of the tube which is between 10 Å and 2000 Å thick and allows the assembly to be bonded together using solvent adhesives. The tubing with the plasma coating from methane and oxygen, which now coats the OD of the tubing, can then cut into lengths for assembly into catheters.

For tubing that has a needle inserted in the tube and the hub, such as an infusion cannula, the polyethylene tube ID must provide a radial force on the needle joint and the ID of the tube should be selected such that for a needle OD of 0.016 to 0.017 inches, the tube ID is 0.014 to 0.015 inches, and for a needle OD of 0.018 to 0.019 inches, the tube ID is 0.016 to 0.017 inches. This provides a slight press fit to the needle. The press fit of the needle caused by this procedure seals the needle to the inner tube and the solvent bonding of the needle and tube to the PVC hub allows the assemble to be bonded together when the tubing is treated with methane plasma. This reduces the cost of assembling the device and the cost of the molded pieces by eliminating the insert molding operations.

The next step is to apply adhesive to both the exposed portion of the needle and the polyethylene tubing OD. An adhesive such as Loctite 4011, a cyanoacrylate adhesive, is acceptable for this application (any solvent base adhesive can be substituted that is capable of bonding the base material of the socket). The length of application is again significant to provide a completely sealed part and prevent the leakage of either air or medication. The plasma coated tubing joint does provide the same sealing characteristics as a PVC to PVC joint and the surface area required to produce a similar joint requires a minimum of area. The needle joint to the PVC requires an application length of at least 0.002 square inches of surface of the needle. For a 0.016 inch diameter needle the application length would have to be 0.050 inches to seal the needle to the PVC. Sealing the Polyethylene tubing to the PVC needs to have least 0.1 inches by 0.030 inches area to give an appropriate bond to prevent the joint from dislodging from the bond or prevent leakage. For a 0.050-inch OD tube this is the minimum length of adhesive would be at least 0.020 inches long. To achieve a full strength bond the application would require a 0.050-inch depth for a 0.050-inch OD polyethylene tube. The ID of the PVC hub in the area of the needle cannot exceed 0.002 inches greater diameter than the needle and the ID of the PVC hub to the polyethylene tube cannot exceed 0.003 inches greater diameter than the assembled tube and bonded needle.

The plasma process can also be extended to Teflon tubing. The process is identical to the LDPE process except that the engagements must have a larger surface area to achieve a suitable bond. The Teflon tubing to the PVC needs to have least 0.15 inches by 0.035 inches area to give an appropriate bond to prevent the joint from dislodging from the bond or prevent leakage. For a 0.050-inch OD tube the minimum length of adhesive would be at least 0.030 inches long. To achieve a full strength bond the application would require a 0.060-inch depth for a 0.050-inch OD Teflon tube. The ID of the PVC hub in the area of the needle cannot exceed 0.002 inches greater diameter than the needle and the id of the PVC hub to the Teflon tube cannot exceed 0.003 inches greater diameter than the assembled tube and bonded needle.

The tubing is processed with the following process parameters.

Plasma Lot Number: DT 622

Plasma Modification for Polyethylene Tube

Plasma gases were methane (99.0% CP grade, AirProducts) and oxygen (Oxygen-2, Twin City Oxygen) introduced separately to plasma reaction chamber. Gas flow rates were 1.0 sccm for methane and 1.2 sccm for oxygen controlled by Vacuum Gauge Measurement and Monomer Flow Controller (MKS Type 146A). Discharge power was 50 watts with RF generator (50 kHz, RF Group Natural Match Plasma Generator). Initial system pressure was 48 mtorr and plasma system pressure was 60 mtorr. Electrode configuration is a capacitive which two 6-inch squares are placed parallel with 2-inch distance. Polyethylene tube sample (0.016 ID, Part # 10006, Putnam Plastics Corp.) was placed in the middle of two electrodes by a plastic fixture. Total deposition thickness was 50 Å monitored by Deposition Controller (Inficon XTC Deposition Controller). Residence time for this modification was 12 minutes. Adhesion strength between polyethylene tube and polycarbonate holder and met the requirement ISO 10555 Sterile, single use intravascular catheters (Part 1: General Requirements). The minimum workable thickness is 10 Å and the maximum deposition useable with this process is 2000 Å.

Plasma Lot Number: DT 625

Material: Polyethylene Sheet and Tube

Plasma gases were methane and oxygen. Gas flow rates were 6.0 sccm for methane and 1.0 sccm for oxygen were fed and controlled by Vacuum Gauge Measurement and Flow Controller. Discharge power was 50 watts. Initial system pressure was 67 mtorr and plasma system pressure was 104 mtorr. Electrode configuration is a capacitive which two 6-inch squares are placed parallel with 2-inch distance. Polyethylene sheet samples were placed in the middle of two electrodes by a plastic fixture. Total deposition thickness was 40 Å monitored by the deposition monitor. Residence time for this modification was 20 minutes. Adhesion strength between polyethylene tube and polycarbonate holder were remarkably improved and met the requirement ISO 10555 Sterile, single use intravascular catheters (Part 1:

General Requirements). The minimum workable thickness is 10 Å and the maximum deposition useable with this process is 2000 Å.

Plasma Lot Number: DT 635

Plasma Modification for Polytetrafluoroethyene Sheet and Tube

Plasma gases were methane and oxygen introduced separately to plasma reaction chamber. Gas flow rates were 6.0 sccm for methane and 4.0 sccm for oxygen controlled by Vacuum Gauge Measurement and Mass Flow Controller. Discharge power was 75 watts. Initial system pressure was 97 mtorr and plasma system pressure was 124 mtorr. Electrode configuration is a capacitive which two 6-inch squares are placed parallel with 2-inch distance. Polytetrafluoroethylene sheet and tube samples were placed in the middle of two electrodes by a plastic fixture. Total deposition thickness was 150 Å monitored by Deposition Controller. Residence time for this modification was 30 minutes. Adhesion strength between polytetrafluoroethylene tube and polycarbonate holder were remarkably improved and met the requirement ISO 10555 Sterile, single use intravascular catheters (Part 1: General Requirements). The minimum workable thickness is 10 Å and the maximum deposition useable with this process is 2000 Å.

An excellent reference on materials and process for fabricating electronic components is Charles A. Harper, Handbook of Materials and Processes for Electronics, 1984, Library of Congress card number 76-95803. It provides detail process information on plasma gas processes.

The process works for either tubing or sheet.

These and other advantages of the present invention are all obtained without incurring any relative disadvantage.

BRIEF DESCRIPTION OF THE DRAWINGS

These and other advantages of the present invention are best understood with reference to the drawings, in which.

DETAILED DESCRIPTION OF THE PREFERRED EMBODIMENT

Figure 1:
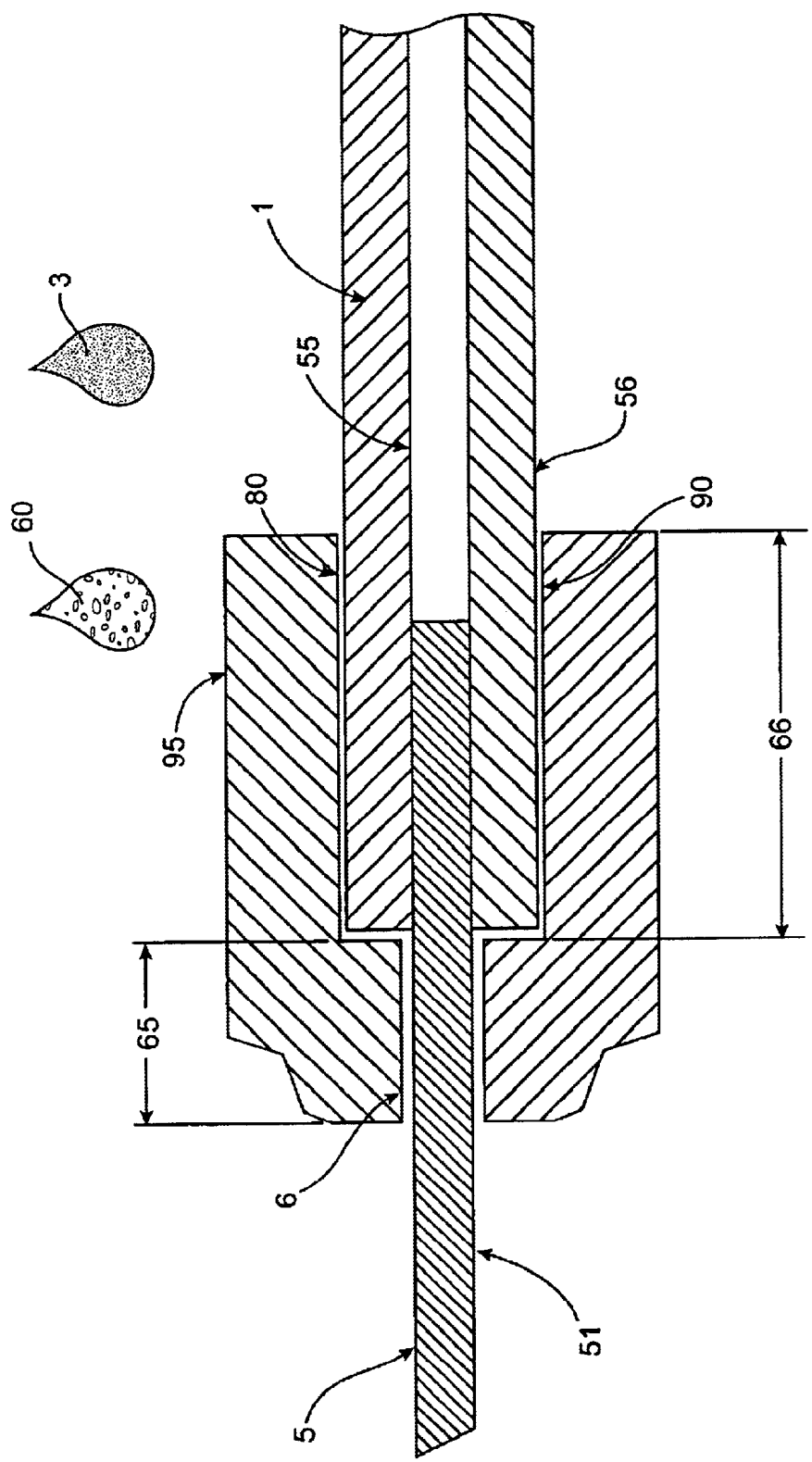
FIG. 1 is an elevation view showing the needle hub and polyethylene or polypropylene tube bonding locations when used with a polymer primer.

Referring to FIG. 1, an elevation view of a first embodiment of the injection set 1 of the present invention.

The means of insuring this is to utilize a process that achieves a double containment and utilizes a suitable primer such as Loctite 7701 or LDPE primer from Toagosei that enables the solvent bonding of the polyethylene or polypropylene tube to the PVC hub. Loctite 7701 and the LDPE primer from Toagosei are solutions of aliphatic amine in Heptane solvent. An adhesive such as Loctite 4011 is acceptable for this application (any solvent base adhesive can be substituted that is capable of bonding the base material of the socket).

The tubing 1 is first treated on the OD with a primer 3 such as Loctite 7701 or LDPE primer from Toagosei and the PVC or PC hub ID 95 is also treated with the same primer 3. This is not obvious because the instructions for the primer 3 do not identify coating the ID 80 of the solvent bondable hub 95. The solvent adhesive 60 is applied to the OD 56 of the tubing 1 and the joint is bonded together by pushing the tubing 1 into the socket 90 and twisting the tube while inserting one revolution. Solvent adhesive 60 can be Loctite 4011 (however, any solvent base adhesive can be substituted that is capable of bonding the base material of the socket) By twisting the tube it spreads the primer/adhesive mix so it is evenly distributed to get the best bond. This process provides a suitable bond between the tubing 1 and the PVC or PC hub 95. The pull test results for the process described versus applying the primer to only the OD 56 of the LDPE tubing 1 and following the same procedure is 15 out of 15 bonds were seal correctly so they were leak tight vs. 3 out of 15 for the traditional process. However, to insure that the joint worked even with the modified process the dimensions of the socket and the fit of the tube had to meet the following dimensional requirements.

For tubing 1 that has a needle 5 inserted in the tube 1 and the hub 95 such as an infusion cannula, the polyethylene tube ID 55 must provide a radial force on the needle joint 6 and the ID of the tube 55 should be selected such that for a needle OD 51 of 0.016 to 0.017 inches, the tube 1 ID 55 is 0.015 to 0.014 inches, and for a needle OD 51 of 0.018 to 0.019 inches, the tube ID 55 is 0.016 to 0.017 inches. This provides a slight press fit to the needle 5. The press fit of the needle 5 caused by this procedure seals the needle 5, to the inner diameter of the tube 55 and the solvent boding of the needle OD 51 and tube OD 56 to the PVC or PC hub 95 allows the assemble to be bonded together when the tubing 1 is treated with primer 3. This reduces the cost of assembling the device and the cost of the molded pieces by eliminating the insert molding operations.

The next step is to apply the primer 3 such as Loctite 7701 or LDPE primer from Toagosei as describe above to both the ID of the hub 95 socket 80 and the OD of the polyethylene tubing 56. The adhesive 60 such as Loctite 4011 (any solvent base adhesive can be substituted that is capable of bonding the base material of the socket) must be applied and the join made up within 3 minutes of the application of the primer so as not to dry out the primed surface. The Loctite 4011 adhesive 60 is an acceptable adhesive for this application. The length of application is again significant to provide a completely sealed part and prevent the leakage of either air or medication. The primer coated tubing joint does provide the same sealing characteristics as a PVC to PVC joint and the surface area required to produce a similar joint requires a minimum of area. The needle joint 6 to the PVC hub 95 requires an application length of at least 0.002 square inches of surface of the needle 5. For a 0.016 inch diameter needle 5 the application length 65 would have to be 0.050 inches. Sealing the needle 5 to the PVC or PC and the Polyethylene tubing 1 to the PVC socket 80 application length 66 needs to have least 0.1 inches by 0.030 inches area to give an appropriate bond to prevent the joint from dislodging from the bond or prevent leakage. For a 0.050-inch ID tube 1 the minimum length of adhesive would be at least 0.10 inches long. The equation for the hub socket size is: minimum area to seal=OD of tube 56/16.67 or minimum socket length 66=2 * OD 56, the fully effective length is 2.6 * OD 56. To achieve a full strength bond the application would require a 0.130 inch depth for a 0.050-inch OD polyethylene tube. The ID 80 of the PVC hub 95 in the area of the needle cannot exceed 0.002 inches greater diameter than the needle OD 51 and the ID 80 of the PVC hub 95 to the polyethylene tube OD 56 cannot exceed 0.003 inches greater diameter than the assembled tube and bonded needle. If the dimensional requirements are not met the bond shear strength is not adequate to meet the ISO requirements and the tubing can be pulled out of the socket or the needle pulled out of the tube.

The press fit of the needle caused by this procedure seals the needle to the inner tube and the solvent boding of the needle and tube to the PVC hub allows the assembly to be bonded together when the tubing is treated with the primer. This reduces the cost of assembling the device and the cost of the molded pieces by eliminating the insert molding operations.

Figure 2:
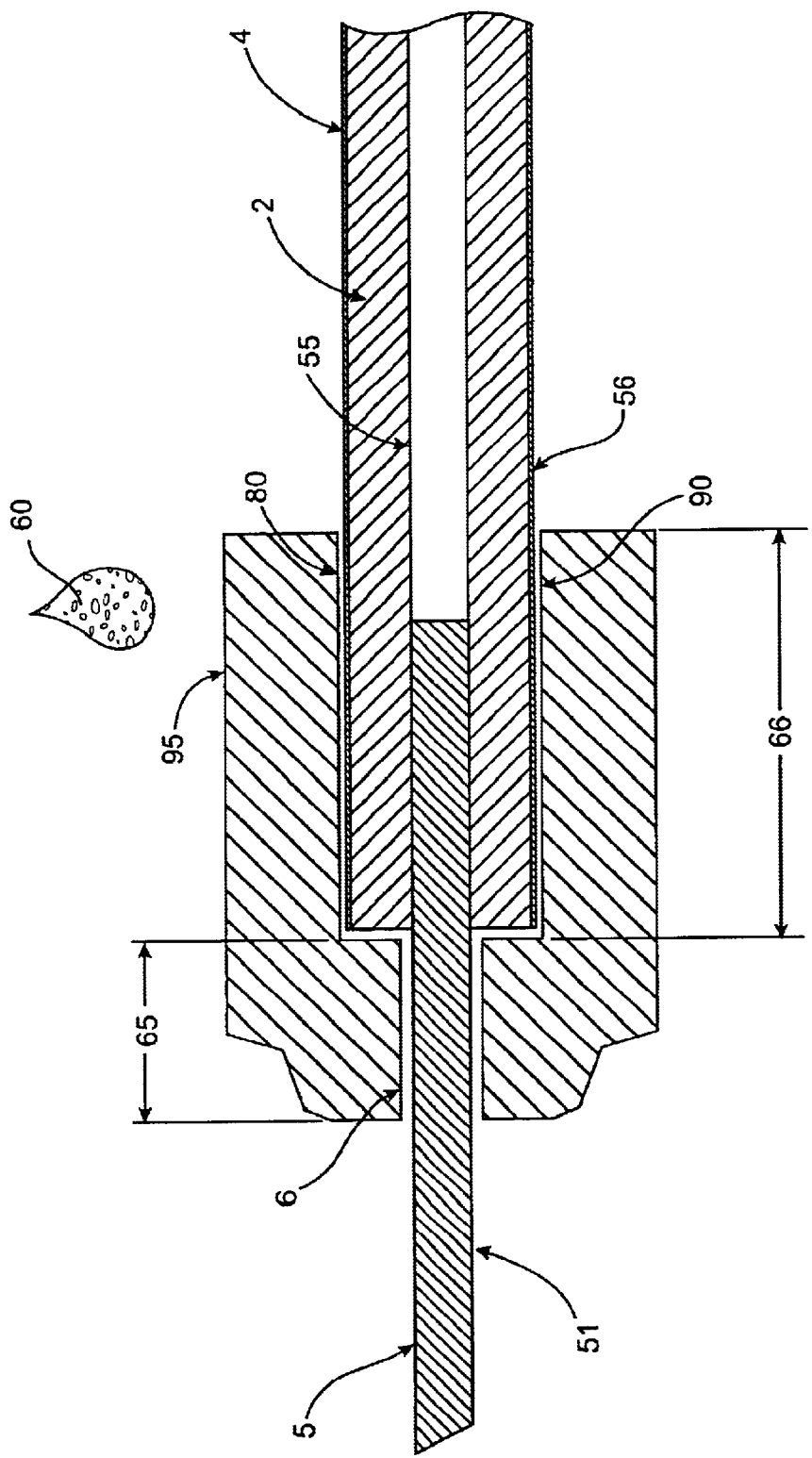
FIG. 2 is an elevation view showing the needle hub and polyethylene or polypropylene tube bonding locations when used with a plasma process.

Referring to FIG. 2, an elevation view of a next embodiment of the injection set 2 of the present invention.

The means of insuring this is to utilize a process that achieves a double containment and utilizes a plasma discharged layer that enables the solvent bonding of the polyethylene or polypropylene tube to the PVC hub without a primer. An adhesive such as Loctite 4011 is acceptable for this application (any solvent base adhesive can be substituted that is capable of bonding the base material of the socket).

The OD 56 of the tubing 2 must be plasma pretreated with methane and oxygen to provide a surface boundary 4 that allows for solvent bonding. The methane and oxygen surface boundary 4 adheres to the OD 56 of the tube 2 and provides an outer surface that is receptive to the solvent bonding. The treatment of the OD 56 of the tube 2 can be completed in a batch method in a suitable plasma coating system. The preferred process is to use plasma coating with the gases methane and oxygen. Gas flow rates were 6.0 sccm for methane and 1.0 sccm for oxygen were fed and controlled by Vacuum Gauge Measurement and Flow Controller. Discharge power was 50 watts. Initial system pressure was 67 mtorr and plasma system pressure was 104 mtorr. Electrode configuration is a capacitive which two 6-inch squares are placed parallel with 2-inch distance. Polyethylene tubing is placed in the middle of two electrodes by a plastic fixture. Total deposition thickness was 40 Å monitored by the deposition monitor. Residence time for this modification was 20 minutes. The minimum workable thickness is 10 Å and the maximum deposition useable with this process is 2000 Å.

For tubing 2 that has a needle 5 inserted in the tube 1 and the hub 95 such as an infusion cannula the polyethylene tube ID 55 must provide a radial force on the needle joint 6 and the ID of the tube 55 should be selected such that for a needle OD 51 of 0.016 to 0.017 inches, the tube ID 55 is 0.015 to 0.014 inches, for a needle OD 51 of 0.018 to 0.019 inches, the tube ID 55 is 0.016 to 0.017 inches. This provides a slight press fit to the needle 5. The press fit of the needle 5 caused by this procedure seals the needle 5 to the inner diameter of the tube 55 and the solvent boding of the needle OD 51 and tube OD 56 to the PVC or PC hub 95 allows the assembly to be bonded together when the tubing 2 is treated with methane plasma 93. This reduces the cost of assembling the device and the cost of the molded pieces by eliminating the insert molding operations.

The adhesive 60 such as Loctite 4011 (any solvent base adhesive can be substituted that is capable of bonding the base material of the socket) must be applied and the join made up within 3 minutes of the application of the primer so as not to dry out the primed surface. The Loctite 4011 adhesive 60 is an acceptable adhesive for this application. The length of application is again significant to provide a completely sealed part and prevent the leakage of either air or medication. The plasma coated tubing joint does provide the same sealing characteristics as a PVC to PVC joint and the surface area required to produce a similar joint requires a minimum of area. The needle joint 6 to the PVC hub 95 requires an application length of at least 0.002 square inches of surface of the needle 5. For a 0.016 inch diameter needle 5 the application length 65 would have to be 0.050 inches to seal the needle 5 to the PVC or PC and the Polyethylene tubing 1 to the PVC socket 80 application length 66 needs to have least 0.2 inches by 0.040 inches area to give an appropriate bond to prevent the joint from dislodging from the bond or prevent leakage. For a 0.050-inch ID tube 2 the minimum length of adhesive would be at least 0.095 inches long. To achieve a full strength bond the application would require a 0.080-inch depth for a 0.050-inch OD polyethylene tube. The equation for the hub socket size is: minimum area to seal=OD of tube 56/6.25 or minimum socket length 66=1 * OD 56, the fully effective length is 1.6 * OD 56. The ID 6 of the PVC hub 95 in the area of the needle cannot exceed 0.002 inches greater diameter than the needle OD 51 and the ID 80 of the PVC hub 95 to the polyethylene tube OD 56 cannot exceed 0.003 inches greater diameter than the assembled tube and bonded needle. If the dimensional requirements are not met the bond shear strength is not adequate to meet the ISO requirements and the tubing can be pulled out of the socket or the needle pulled out of the tube.

Figure 3:
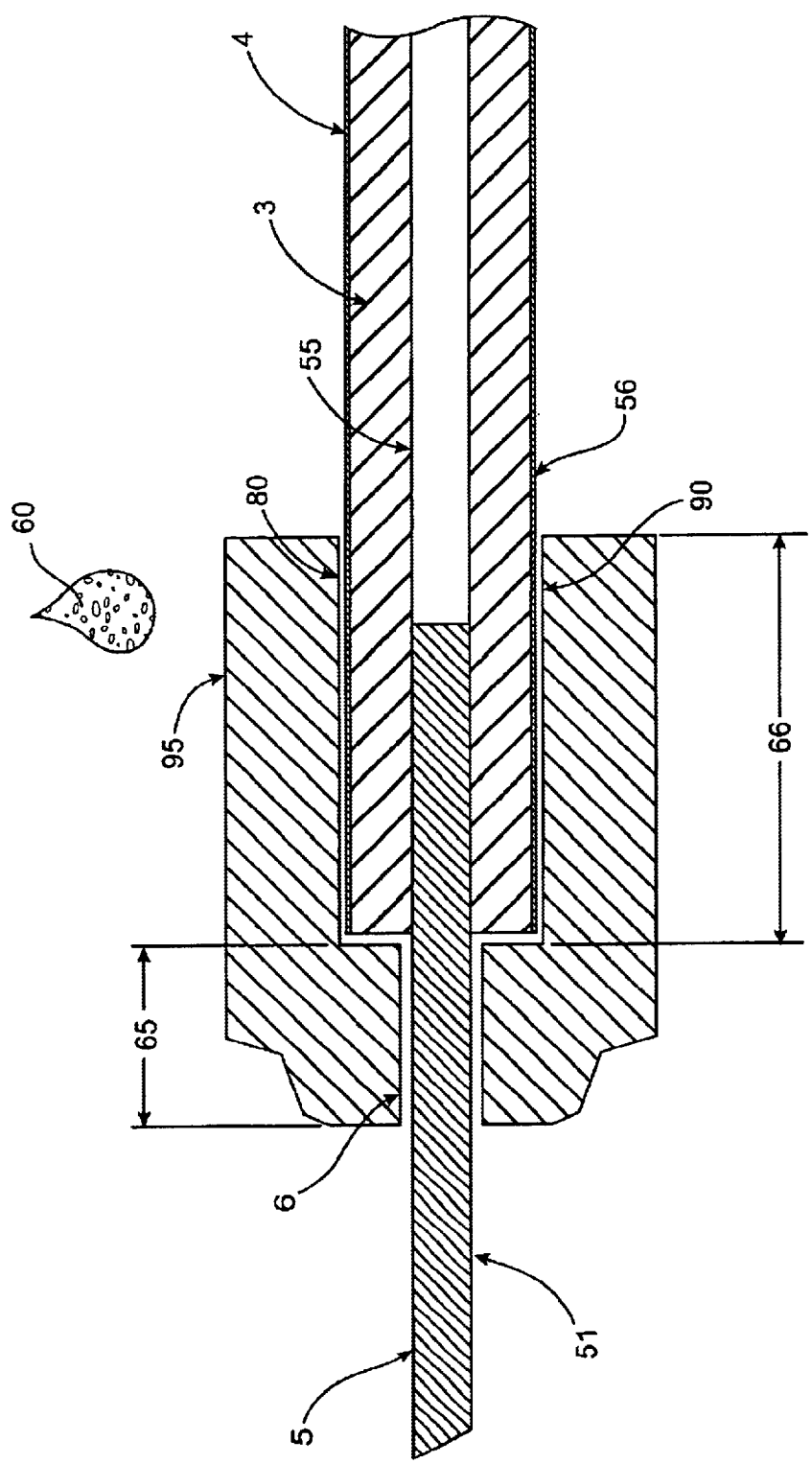
FIG. 3 is an elevation view showing the needle hub and Polytetrafluoroethyene tube bonding locations when used with a plasma process.

Referring to FIG. 3, an elevation view of a next embodiment of the injection set 3 of the present invention.

The means of insuring this is to utilize a process that achieves a double containment and utilizes a plasma discharged layer that enables the solvent bonding of the Polytetrafluoroethyene tube 3 to the PVC hub without a primer. An adhesive such as Loctite 4011 is acceptable for this application (any solvent base adhesive can be substituted that is capable of bonding the base material of the socket).

The OD 56 of the tubing 3 must be plasma pretreated with methane and oxygen to provide a surface boundary 4 that allows for solvent bonding. The methane surface boundary 2 adheres to the OD 56 of the tube 3 and provides an outer surface that is receptive to the solvent bonding. The treatment of the OD 56 of the tube 3 can be completed in a batch method in a suitable plasma coating system. The preferred process is to use plasma coating with the gases methane and oxygen. Gas flow rates were 6.0 sccm for methane and 1.0 sccm for oxygen were fed and controlled by Vacuum Gauge Measurement and Flow Controller. Discharge power was 50 watts. Initial system pressure was 67 mtorr and plasma system pressure was 104 mtorr. Electrode configuration is a capacitive which two 6-inch squares are placed parallel with 2-inch distance. Polytetrafluoroethyene samples were placed in the middle of two electrodes by a plastic fixture. Total deposition thickness was 150 Å monitored by the deposition monitor. Residence time for this modification was 30 minutes. The minimum workable thickness is 10 Å and the maximum deposition useable with this process is 2000 Å.

For tubing 3 that has a needle 5 inserted in the tube 3 and the hub 95 such as an infusion cannula, the Polytetrafluoroethyene tube ID 55 must provide a radial force on the needle joint 6 and the ID of the tube 55 should be selected such that for a needle OD 51 of 0.016 to 0.017 inches, the tube ID 55 is 0.015 to 0.014 inches, and for a needle OD 51 of 0.018 to 0.019 inches, the tube ID 55 is 0.016 to 0.017 inches. This provides a slight press fit to the needle 5. The press fit of the needle 5 caused by this procedure seals the needle 5 to the inner diameter of the tube 55 and the solvent boding of the needle OD 51 and tube OD 56 to the PVC or PC hub 95 allows the assemble to be bonded together when the tubing 3 is treated with methane plasma 93. This reduces the cost of assembling the device and the cost of the molded pieces by eliminating the insert molding operations.

The adhesive 60 such as Loctite 4011 (any solvent base adhesive can be substituted that is capable of bonding the base material of the socket) must be applied and the join made up within 3 minutes of the application of the primer to prevent the primed surface from drying out. The Loctite 4011 adhesive 60 is an acceptable adhesive for this application. The length of application is again significant to provide a completely sealed part and prevent the leakage of either air or medication. The plasma coated tubing joint does provide the same sealing characteristics as a PVC to PVC joint and the surface area required to produce a similar joint requires a minimum of area. The needle joint 6 to the PVC hub 95 requires an application length of at least 0.002 square inches of surface of the needle 5. For a 0.016 inch diameter needle 5 the application length 65 would have to be 0.050 inches to seal the needle 5 to the PVC or PC and the Polytetrafluoroethyene tubing 3 to the PVC socket 80 application length 66 needs to have least 0.3 inches by 0.050 inches area to give an appropriate bond to prevent the joint from dislodging from the bond or prevent leakage. For a 0.050-inch ID tube 3 the minimum length of adhesive would be at least 0.095 inches long. To achieve a full strength bond the application would require a 0.140 inch depth for a 0.050-inch OD polyethylene tube. The equation for the hub socket size is: minimum area to seal=OD of tube 56/3.33 or minimum socket length 66=1.9 * OD 56, the fully effective length is 2.8* OD 56. The ID 80 of the PVC hub 95 in the area of the needle cannot exceed 0.002 inches greater diameter than the needle OD 51 and the ID 80 of the PVC hub 95 to the polyethylene tube OD 56 cannot exceed 0.003 inches greater diameter than the assembled tube and bonded needle. If the dimensional requirements are not met the bond shear strength is not adequate to meet the ISO requirements and the tubing can be pulled out of the socket or the needle pulled out of the tube.

The press fit of the needle caused by this procedure seals the needle to the inner tube and the solvent bonding of the needle and tube to the PVC hub allows the assemble to be bonded together when the tubing is treated with the plasma coating. This reduces the cost of assembling the device and the cost of the molded pieces by eliminating the insert molding operations.

Because of the simplicity of the preferred embodiment of the injection set described above, it is adaptable to use as a disposable device which may be conveniently used by the patient without need to be concerned with the sterility of the prefilled medication. A typical use of the injection set will be by diabetics who receive a controlled dose of insulin from an external insulin delivery system.

Figure 4:
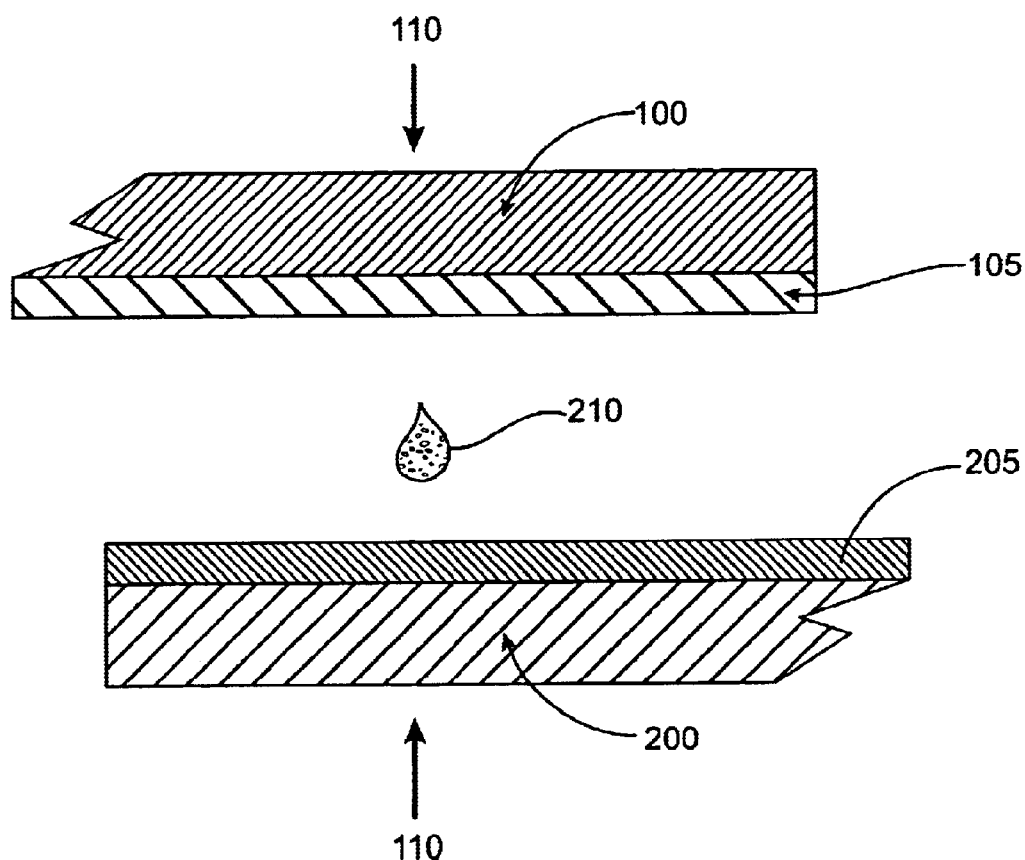
FIG. 4 is an elevation view of a sheet with plasma coating bonded to a second part with plasma coating.

FIG. 4 shows an alternate use for the invention is to provide a bondable surface between two sheets or parts of dissimilar materials that do not solvent bond. Examples of this are Teflon sheet to Teflon sheet or LDPE sheet to LDPE sheet or either LDPE or Teflon sheet to a PVC part. To accomplish this the sheets to be bonded are treated accordingly and the solvent adhesive is applied to the joint and the two parts are secured by placing them in contact and applying pressure to the to opposing sides of the joint.

Creating a boundary layer for Low Density Polyethylene (LDPE) sheet the plasma gases are methane and oxygen. Gas flow rates were 6.0 sccm for methane and 1.0 sccm for oxygen were fed and controlled by Vacuum Gauge Measurement and Flow Controller. Discharge power was 50 watts. Initial system pressure was 67 mtorr and plasma system pressure was 104 mtorr. Electrode configuration is a capacitive which two 6-inch squares are placed parallel with 2-inch distance. Polyethylene sheet samples were placed in the middle of two electrodes by a plastic fixture. Total deposition thickness was 40 Å monitored by the deposition monitor. Residence time for this modification was 20 minutes. The minimum workable thickness is 10 Å and the maximum deposition useable with this process is 2000 Å.

Creating a boundary layer for Polytetrafluoroethyene sheet (Teflon) the plasma gases are methane and oxygen introduced separately to plasma reaction chamber. Gas flow rates were 6.0 sccm for methane and 4.0 sccm for oxygen controlled by Vacuum Gauge Measurement and Mass Flow Controller. Discharge power was 75 watts. Initial system pressure was 97 mtorr and plasma system pressure was 124 mtorr. Electrode configuration is a capacitive which two 6-inch squares are placed parallel with 2-inch distance. Polytetrafluoroethylene sheet samples are placed in the middle of two electrodes by a plastic fixture. Total deposition thickness was 150 Å monitored by Deposition Controller. Residence time for this modification was 30 minutes. The minimum workable thickness is 10 Å and the maximum deposition useable with this process is 2000 Å.

The plasma coated sheet 100 has plasma treated deposit 105 applied per the process defined above and the second plasma coated sheet 200 with a plasma treated deposit 205 is positioned to be joined. An adhesive 210 such as Loctite 4011, a cyanoacrylate adhesive, is applied per the manufactures recommendation for bonding solvent bondable materials and pressure 110 is applied to the opposing sides of the joint to secure the two parts together. Solvent bonding occurs between the 2-deposited plasma layers 105 and 205. However, the bond that results from the plasma coated sheets 100 and 200 with plasma treated deposits 105 and 205 has a joint shear strength of approximately 80% of a conventional solvent bonded joint.

Figure 5:
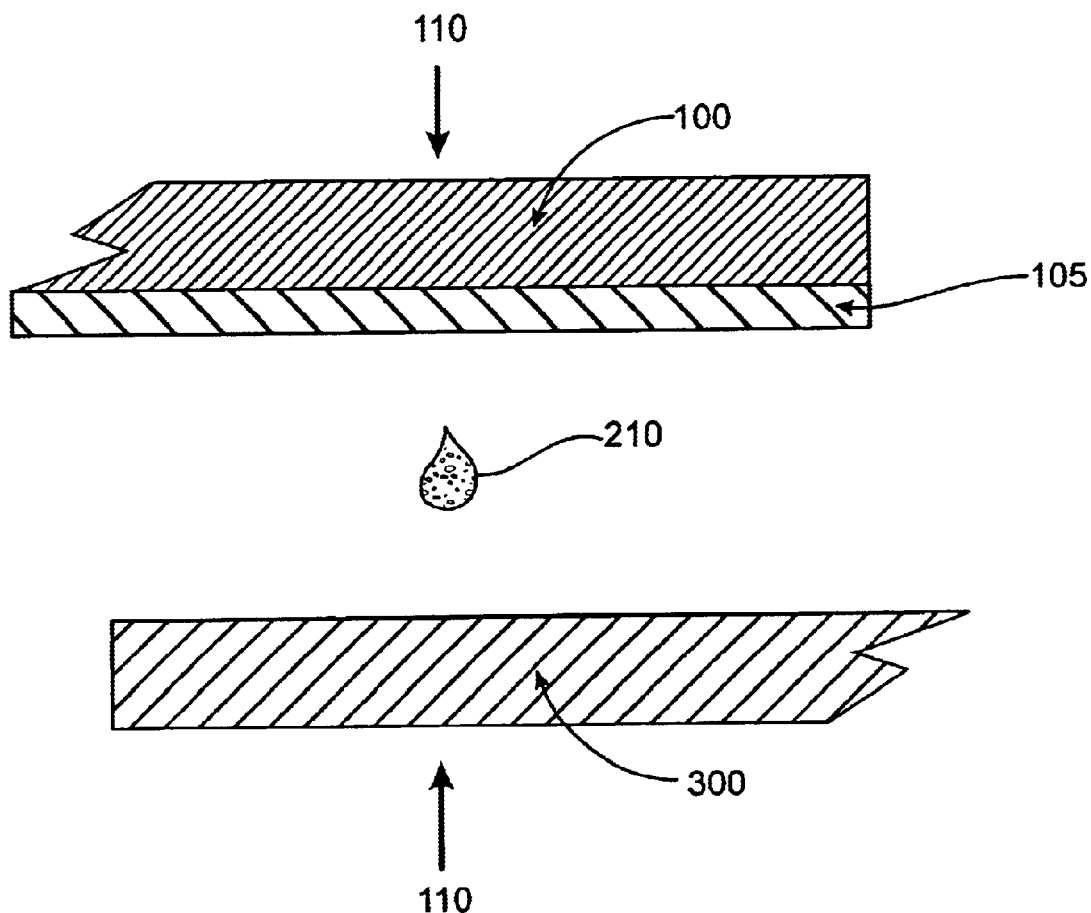
FIG. 5 is an elevation view of a sheet with plasma coating bonded to a solvent bondable part.

FIG. 5 shows an alternate use for the invention is to provide a bondable surface between two sheets or parts of dissimilar materials that do not solvent bond. Examples of this are Teflon sheet to a PVC sheet or part or LDPE sheet to a PVC sheet or part. To accomplish this the sheet to be bonded is treated accordingly and the solvent adhesive is applied to the joint and the two parts are secured by placing them in contact and applying pressure to the to opposing sides of the joint.

Creating a boundary layer for Low Density Polyethylene (LDPE) sheet, the plasma gases are methane and oxygen. Gas flow rates were 6.0 sccm for methane and 1.0 sccm for oxygen were fed and controlled by Vacuum Gauge Measurement and Flow Controller. Discharge power was 50 watts. Initial system pressure was 67 mtorr and plasma system pressure was 104 mtorr. Electrode configuration is a capacitive which two 6-inch squares are placed parallel with 2-inch distance. Polyethylene sheet samples were placed in the middle of two electrodes by a plastic fixture. Total deposition thickness was 40 Å monitored by the deposition monitor. Residence time for this modification was 20 minutes. The minimum workable thickness is 10 Å and the maximum deposition useable with this process is 2000 Å.

Creating a boundary layer for Polytetrafluoroethyene sheet (Teflon) the plasma gases are methane and oxygen introduced separately to plasma reaction chamber. Gas flow rates were 6.0 sccm for methane and 4.0 sccm for oxygen controlled by Vacuum Gauge Measurement and Mass Flow Controller. Discharge power was 75 watts. Initial system pressure was 97 mtorr and plasma system pressure was 124 mtorr. Electrode configuration is a capacitive which two 6-inch squares are placed parallel with 2-inch distance. Polytetrafluoroethylene sheet samples are placed in the middle of two electrodes by a plastic fixture. Total deposition thickness was 150 Å monitored by Deposition Controller. Residence time for this modification was 30 minutes. The minimum workable thickness is 10 Å and the maximum deposition useable with this process is 2000 Å.

The plasma coated sheet 100 has plasma treated deposit 105 applied per the process defined above and the solvent bondable material 300 is positioned to be joined. An adhesive 210 such as Loctite 4011, a cyanoacrylate adhesive, is applied per the manufactures recommendation for bonding solvent bondable materials and pressure 110 is applied to the opposing sides of the joint to secure the two parts together. Solvent bonding occurs between the deposited plasma layer 105 and the solvent bondable material. However, the bond that results from the plasma coated sheets 100 with plasma treated deposit 105 and the solvent bondable material has a joint shear strength of approximately 85% of a conventional solvent bonded joint.

The invention has been described with reference to a preferred embodiment. Many modifications can be carried out without thereby deviating from the scope of the invention.

While the invention herein disclosed has been described by means of a specific preferred embodiment and applications thereof, numerous modifications and variations could be made thereto by those skilled in the art without departing from the spirit and scope of the present invention. It is therefore to be understood that within the scope of the appended claims, the invention may be practiced otherwise than as specifically described herein.

What is claimed is:

1. A cyanoacrylate adhesive bondable joint comprising:
   a LDPE part having a plasma deposited layer of methane and oxygen gas;
   a cyanoacrylate adhesive applied to the joint;
   a cyanoacrylate adhesive bondable piece in communication with the cyanoacrylate adhesive; and
   wherein the plasma polymer layer of methane is at least 10 Å thick but not greater than 2000 Å.

2. A cyanoacrylate adhesive bondable joint comprising:
   a polytetrafluoroethylene part having a plasma deposited layer of methane and oxygen gas;
   a cyanoacrylate adhesive applied to the joint;
   a cyanoacrylate adhesive bondable piece in communication with the cyanoacrylate adhesive; and
   wherein the plasma polymer layer of methane is at least 10 Å thick but not greater than 2000 Å.

3. A cyanoacrylate adhesive bondable joint comprising:
   a LDPE part having a plasma deposited layer of methane and oxygen gas;
   a cyanoacrylate adhesive applied to the joint;
   a LDPE part having a plasma deposited layer of methane and oxygen gas in communication with the cyanoacrylate adhesive; and
   wherein the plasma polymer layer of methane is at least 10 Å thick but not greater than 2000 Å.

4. A cyanoacrylate adhesive bondable joint comprising:
   a polytetrafluoroethylene part having a plasma deposited layer of methane and oxygen gas
   a cyanoacrylate adhesive applied to the joint;
   a polytetrafluoroethylene part having a plasma deposited layer of methane and oxygen gas in communication with the cyanoacrylate adhesive; and
   wherein the plasma polymer layer of methane is at least 10 Å thick but not greater than 2000 Å.

5. A cyanoacrylate adhesive bondable joint comprising:
   a LDPE part having a plasma deposited layer of methane and oxygen gas;
   a cyanoacrylate adhesive applied to the joint;
   a polytetrafluoroethylene part having a plasma deposited layer of methane and oxygen gas in communication with the cyanoacrylate adhesive; and
   wherein the plasma polymer layer of methane is at least 10 Å thick but not greater than 2000 Å.

* * * * *

UNITED STATES PATENT AND TRADEMARK OFFICE
CERTIFICATE OF CORRECTION

PATENT NO. : 6,673,440 B2
DATED : January 6, 2004
INVENTOR(S) : Joel Sterling Douglas, Robert Louis Hugo and Hiroshi Nomura It is certified that error appears in the above-identified patent and that said Letters Patent is hereby corrected as shown below:

<u>Title page,</u>
Item [75], Inventors, please delete "Nomvra" and insert -- Nomura -- in place thereof.

Signed and Sealed this

Twenty-fifth Day of May, 2004

JON W. DUDAS
*Acting Director of the United States Patent and Trademark Office*